United States Patent
Saito et al.

(10) Patent No.: US 9,867,598 B2
(45) Date of Patent: Jan. 16, 2018

(54) FECES SAMPLING CONTAINER

(71) Applicants: EIKEN KAGAKU KABUSHIKI KAISHA, Tokyo (JP); TOYO SEIKAN CO., LTD., Tokyo (JP)

(72) Inventors: Shingo Saito, Tokyo (JP); Yoshiharu Ichikawa, Tokyo (JP); Hiroaki Hayashi, Yokohama (JP); Kazuhiro Toyama, Yokohama (JP); Masashi Ishikawa, Yokohama (JP)

(73) Assignees: EIKEN KAGAKU KABUSHIKI KAISHA, Tokyo (JP); Toyo Seikan Co., Ltd., Tokyo (JP)

( * ) Notice: Subject to any disclaimer, the term of this patent is extended or adjusted under 35 U.S.C. 154(b) by 0 days.

(21) Appl. No.: 15/026,999

(22) PCT Filed: Oct. 2, 2014

(86) PCT No.: PCT/JP2014/005035
§ 371 (c)(1),
(2) Date: Apr. 4, 2016

(87) PCT Pub. No.: WO2015/052901
PCT Pub. Date: Apr. 16, 2015

(65) Prior Publication Data
US 2016/0256136 A1    Sep. 8, 2016

(30) Foreign Application Priority Data

Oct. 10, 2013  (JP) .................................. 2013-212995
Feb. 7, 2014   (JP) .................................. 2014-000610

(51) Int. Cl.
*G01N 21/75*   (2006.01)
*A61B 10/00*   (2006.01)
(Continued)

(52) U.S. Cl.
CPC ...... *A61B 10/0038* (2013.01); *B01L 3/50825* (2013.01); *G01N 1/04* (2013.01);
(Continued)

(58) Field of Classification Search
CPC ... A61B 10/0038; B01L 3/502; B01L 3/5029; B01L 3/5082; B01L 3/50825; B01L 2300/42
(Continued)

(56) References Cited

U.S. PATENT DOCUMENTS 5,246,669 A    9/1993  Hayashi
5,514,341 A    5/1996  Urata et al.
(Continued)

FOREIGN PATENT DOCUMENTS

DE   102008057866 A1   5/2010
EP   2 279 965 A1      2/2011
(Continued)

OTHER PUBLICATIONS

International Preliminary Report on Patentability and Written Opinion issued by the International Bureau of WIPO in corresponding International Application No. PCT/JP2014/005035, dated Apr. 21, 2016.
(Continued)

*Primary Examiner* — Jill Warden
*Assistant Examiner* — Dwayne K Handy
(74) *Attorney, Agent, or Firm* — Sughrue Mion, PLLC (57) ABSTRACT

A feces sampling container includes: a lid (2) that includes a feces sampling rod (2*b*) and a cap (2*a*), a circular protrusion (2*f*); a container body (3); and an inside plug (4) that includes a removal part (4*b*), and a circular protrusion (4*g*), the inside plug (4) being fitted to the inside of the container body (3), a flange (3*c*), an overhang (4*d*) being formed on the outer circumferential surface of the inside plug (4) at a
(Continued)

predetermined position along the circumferential direction so that the overhang (4d) is situated on the flange (3c), a removal mechanism (2e, 4f), and a cam mechanism (2h, 4h) that positions the removal mechanism being formed over the circular protrusion (2f) formed on the inner circumferential surface of the cap (2a) and the circular protrusion (4g) formed on the outer circumferential surface of the inside plug (4).

18 Claims, 11 Drawing Sheets

(51) Int. Cl.
  *B01L 3/00* (2006.01)
  *G01N 1/04* (2006.01)
(52) U.S. Cl.
  CPC . *B01L 2300/042* (2013.01); *B01L 2300/0832* (2013.01); *B01L 2300/0848* (2013.01); *B01L 2300/0858* (2013.01); *B01L 2300/12* (2013.01)
(58) Field of Classification Search
  USPC ................. 422/405, 406, 411, 547, 549, 550
  See application file for complete search history.

(56) References Cited

U.S. PATENT DOCUMENTS

| | | | |
|---|---|---|---|
| 5,882,942 A | | 3/1999 | Kagaya |
| 2008/0034899 A1* | | 2/2008 | Kikuiri ............... A61B 10/0038 73/864.51 |
| 2010/0000341 A1* | | 1/2010 | Hasegawa .......... A61B 10/0038 73/864 |
| 2010/0044337 A1 | | 2/2010 | Shibata et al. |
| 2011/0239793 A1 | | 10/2011 | Ohtsuka et al. |
| 2011/0243816 A1 | | 10/2011 | Shimada |
| 2013/0211286 A1* | | 8/2013 | Lidgard ............. A61B 10/0038 600/562 |

FOREIGN PATENT DOCUMENTS

| | | |
|---|---|---|
| JP | 6-148177 A | 5/1994 |
| JP | 6-148178 A | 5/1994 |
| JP | 6-186227 A | 7/1994 |
| JP | 6-74965 U | 10/1994 |
| JP | 6-317583 A | 11/1994 |
| JP | 7-12808 A | 1/1995 |
| JP | 8-75725 A | 3/1996 |
| JP | 8-189928 A | 7/1996 |
| JP | 8-285845 A | 11/1996 |
| JP | 8-292189 A | 11/1996 |
| JP | 9-54082 A | 2/1997 |
| JP | 10-300643 A | 11/1998 |
| JP | 11-316222 A | 11/1999 |
| JP | 2002-131195 A | 5/2002 |
| JP | 2004-317481 A | 11/2004 |
| JP | 2007-040984 A | 2/2007 |
| JP | 2007-047042 A | 2/2007 |
| JP | 2007-170979 A | 7/2007 |
| JP | 2011-215020 A | 10/2011 |
| WO | 03/068398 A1 | 8/2003 |
| WO | 2008/090806 A1 | 7/2008 |
| WO | 2009/136445 A1 | 11/2009 |
| WO | 2010/067534 A1 | 6/2010 |

OTHER PUBLICATIONS

Extended European Search Report dated Apr. 25, 2017 for corresponding EP 14 853 123.9.

* cited by examiner

FECES SAMPLING CONTAINER

CROSS REFERENCE TO RELATED APPLICATIONS

This application is a National Stage of International Application No. PCT/JP2014/005035 filed Oct. 2, 2014, claiming priority based on Japanese Patent Application Nos. 2013-212995 filed Oct. 10, 2013 and 2014-000610 filed Feb. 7, 2014, the contents of all of which are incorporated herein by reference in their entirety.

TECHNICAL FIELD

The invention relates to a feces sampling container that is used to sample feces that are subjected to fecal examination.

BACKGROUND ART

Conventionally, as a feces sampling container for sampling feces for fecal examination (scatoscopy), various types of feces sampling container have been proposed. Many of these are provided with a lid provided with a feces sampling rod having a helical groove in its front end side and a container body holding a preservation solution (see Patent Document 1, for example).

In such types of feces sampling container, when sampling feces, the lid is removed, and by, for example, thrusting the feces sampling rod into the feces, the feces is scraped off in a helical groove provided in its front end side, and then the feces sampling rod is returned to the inside of the container, and the container is sealed by the lid. As a result, the sampled feces is suspended in a preservation solution held within the container body. The suspension containing the feces is filtered so as to examine the feces. In order to conduct accurate examination, it is required to allow an appropriate amount of feces to be suspended in a preservation solution, i.e. it is required not to allow the amount of feces suspended in a preservation solution to be too large or too small.

Therefore, in many feces sampling containers, when returning the feces sampling rod to which the feces adhere to the inside of the container, the feces sampling rod is inserted through a removal part formed by providing a partition wall in the inside of the container body or by other methods, thereby to remove excess feces. As a result, an appropriate amount of feces can be sampled.

For example, the feces sampling container disclosed in Patent Document 1 has a configuration in which a removal part that removes excess feces that adhere to the feces sampling rod is provided to an inside plug, and positioned inside the container body by inserting the inside plug into the container body.

RELATED ART DOCUMENT

Patent Document

Patent Document 1: JP-A-H09-54082

SUMMARY OF INVENTION

Technical Problem

It is desirable that the above type of feces sampling container be designed so that it is possible to easily remove the lid having the feces sampling rod from the inside plug, and easily and reliably fit the lid to the inside plug while returning the feces sampling rod to the inside of the container after sampling the feces. The inventors of the invention conducted extensive studies, and found that a further improvement is required for the feces sampling container disclosed in Patent Literature 1 from the above point of view.

The invention was conceived in view of the above situation. An object of the invention is to provide a feces sampling container that includes a lid having a feces sampling rod, a container body, and an inside plug (to which the lid is removably fitted and which is provided with a removal part) that is fitted to the inside of the container body, and makes it possible to easily remove the lid having the feces sampling rod from the inside plug, and easily and reliably fit the lid to the inside plug after inserting the feces sampling rod into the inside plug.

Solution to Problem

According to the invention, a feces sampling container includes:

a lid that includes a feces sampling rod and a cap, a circular protrusion being formed on an inner circumferential surface of the cap along a circumferential direction;

a container body that has a tubular shape and opens on a base end; and an inside plug that includes a removal part and a circular protrusion, the circular protrusion being formed on an outer circumferential surface of the inside plug along a circumferential direction, the inside plug being fitted to the inside of the container body through the base end of the container body, a flange being formed along an edge of a base end-side opening of the container body, an overhang being formed on an outer circumferential surface of the inside plug at a predetermined position along a circumferential direction so that the overhang is situated on the flange, a removal mechanism being formed at a lower end of the cap and on an inner circumferential surface of the overhang of the inside plug, and a cam mechanism that positions the removal mechanism being formed over the circular protrusions formed on the inner circumferential surface of the cap and the circular protrusion formed on the outer circumferential surface of the inside plug.

Advantageous Effects of Invention

The invention thus provides a feces sampling container that includes a lid having a feces sampling rod, a container body, and an inside plug (to which the lid is removably fitted and which is provided with a removal part) that is fitted to the inside of the container body, and makes it possible to easily remove the lid having the feces sampling rod from the inside plug, and easily and reliably fit the lid to the inside plug after inserting the feces sampling rod into the inside plug.

DESCRIPTION OF EMBODIMENTS

Preferred embodiments of the invention are described below with reference to the drawings.

Figure 1:
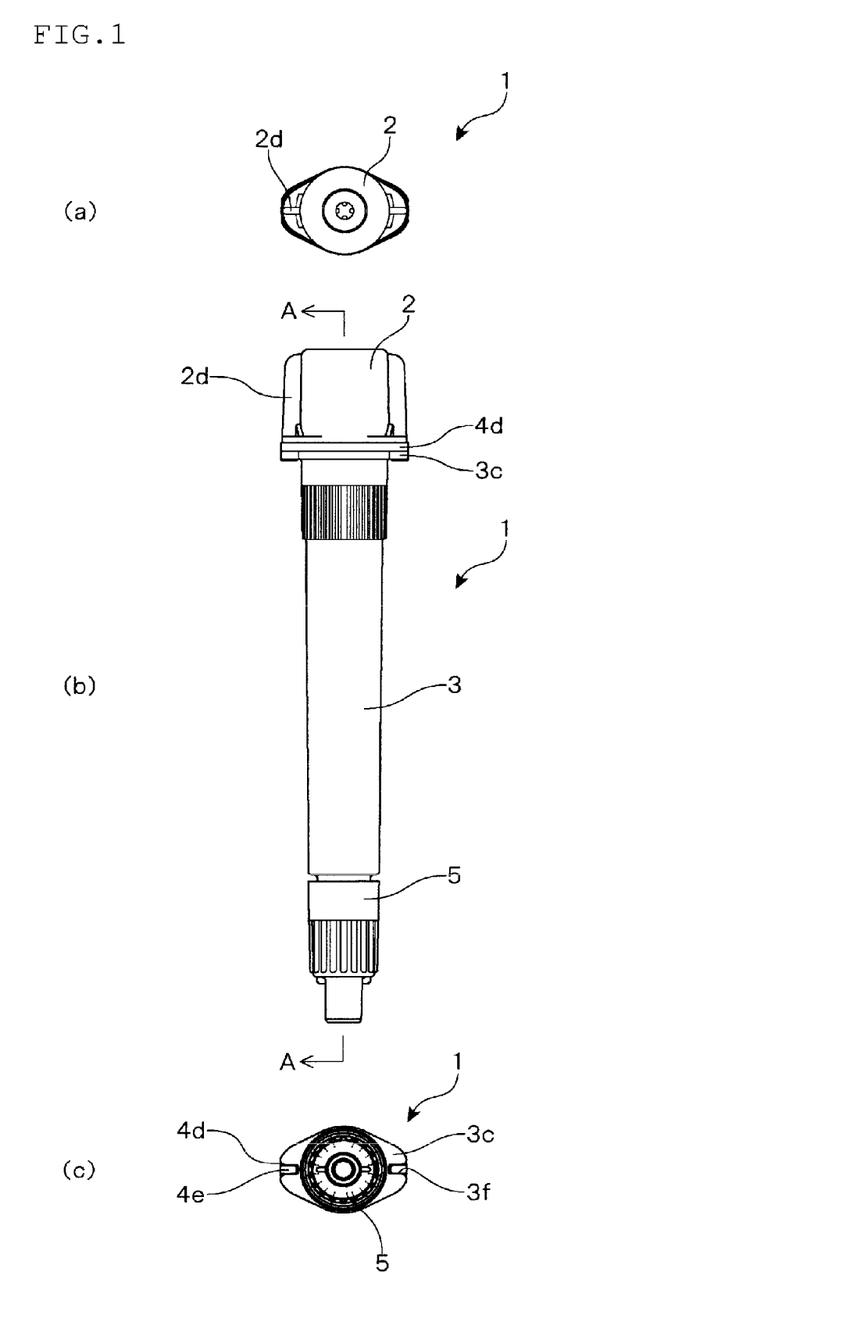
FIG. 1 is a view illustrating a feces sampling container according to one embodiment of the invention, wherein (a) is a plan view, (b) is a front view, and (c) is a bottom view.
Figure 2:
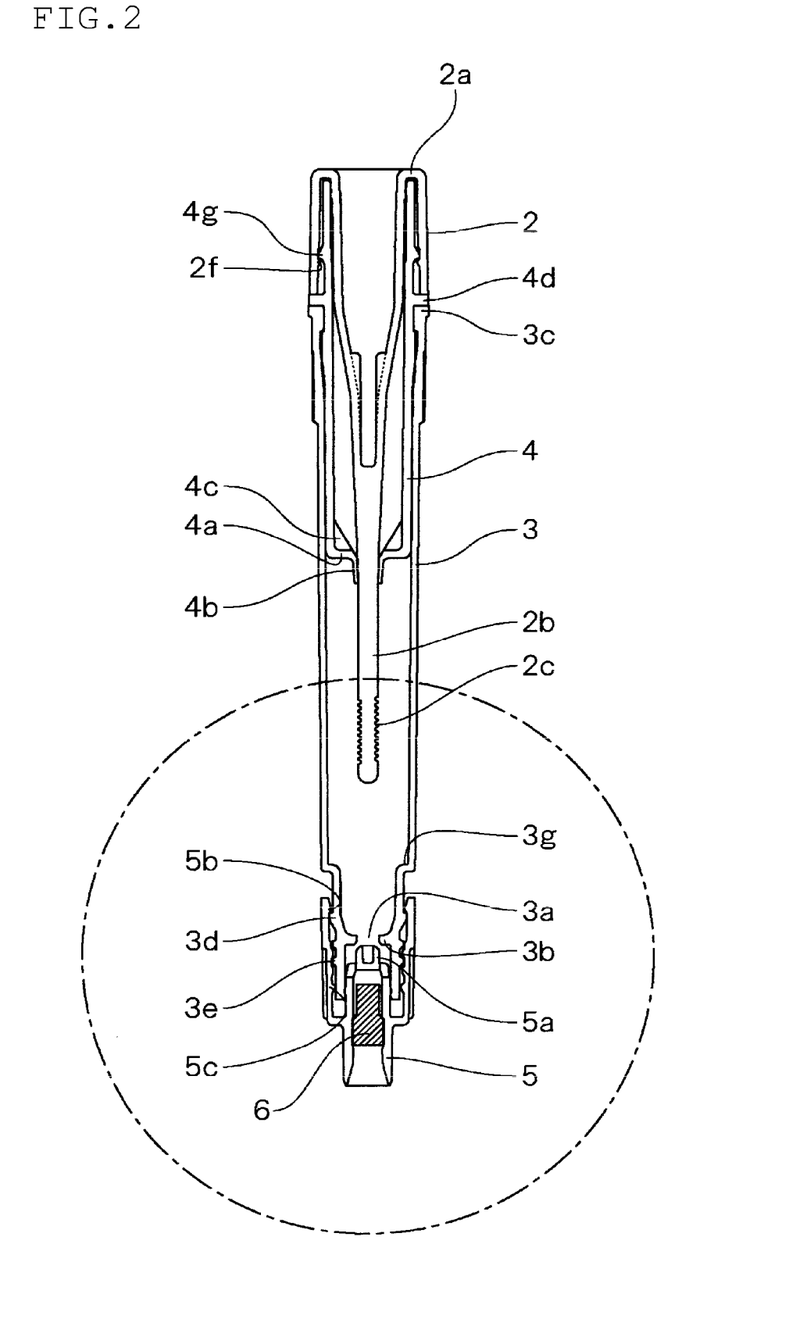
FIG. 2 is a cross-sectional view taken along the line A-A illustrated in FIG. 1 (see (b)).

A feces sampling container 1 according to one embodiment of the invention is used to sample feces that are subjected to fecal examination. As illustrated in FIGS. 1 and 2, the feces sampling container 1 includes a lid 2 that seals the inner space of the feces sampling container 1, a container body 3 that has a tubular shape and holds a preservation solution, an inside plug 4 that is fitted to the inside of the container body 3, and a dropping cap 5 that is screwed to the end of the container body 3.

Figure 3:
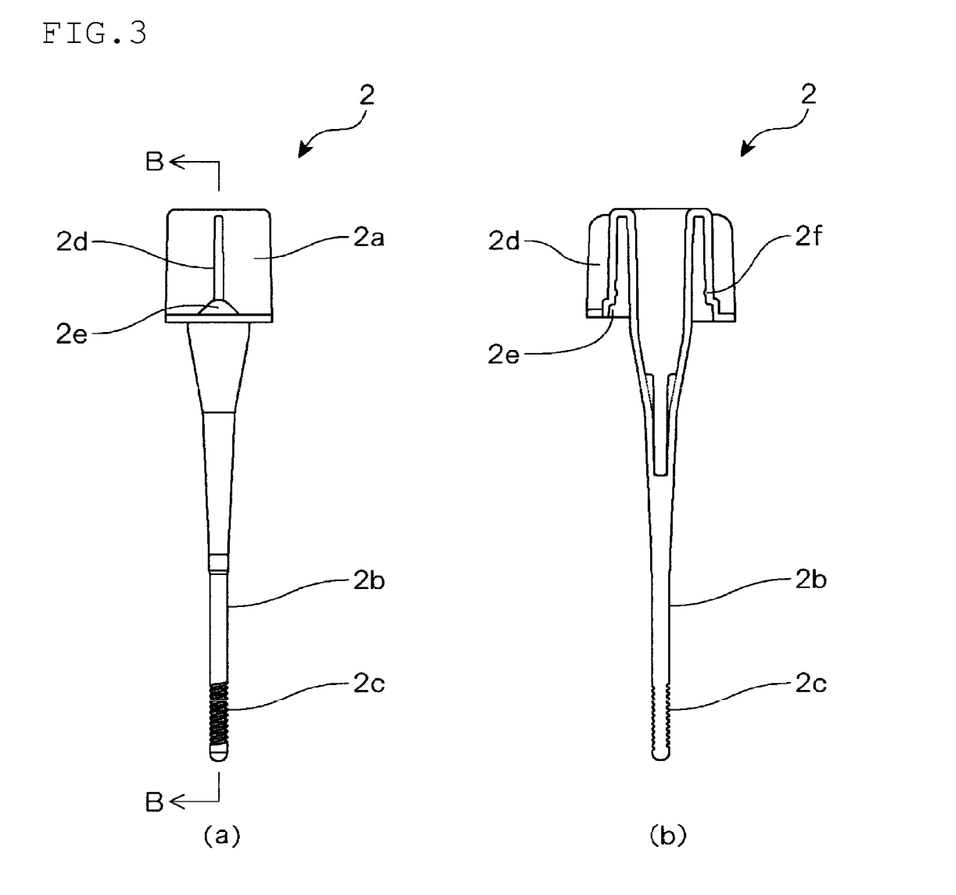
FIG. 3 is a view illustrating an example of a lid included in a feces sampling container according to one embodiment of the invention, wherein (a) is a plan view, and (b) is a cross-sectional view taken along the line B-B (see (a)).

As illustrated in FIG. 3, the lid 2 of the feces sampling container 1 includes a cap 2a that seals the inner space of the feces sampling container 1, and a feces sampling rod 2b for sampling feces. A helical groove 2c is helically formed on the end side of the feces sampling rod 2b. When sampling the feces using the feces sampling rod 2b, the lid 2 is removed from the inside plug 4 that is fitted to the inside of the container body 3, and by, for example, thrusting the feces sampling rod 2b into the feces, the feces is scraped off in the helical groove 2c. After sampling the feces, the lid 2 is fitted to the inside plug 4 and the feces sampling rod 2b is returned to the inside of the container body 3 so that the sampled feces are suspended in the preservation solution held in the container body 3.

In this embodiment, the helical groove 2c is formed on the front end side of the feces sampling rod 2b. The configuration is not limited thereto as long as the feces can be reliably sampled. For example, a plurality of grooves that encircle the feces sampling rod 2b in the direction orthogonal to the longitudinal direction may be provided on the end side of the feces sampling rod 2b. Alternatively, one or more recesses or through-holes having an arbitrary shape may be provided. Various feces sampling tools have been developed for sampling various types of feces (e.g., solid feces, soft feces, and liquid feces).

It is preferable that the feces sampling rod 2b be colored with a color having high brightness (e.g. white or pale color) in order to improve the visibility of the feces that adhere to the feces sampling rod 2b. It is more preferable that the feces sampling rod 2b be colored pale green that is close to the color that is complementary to the color (brown to yellowish brown) of feces.

The lid 2 of the feces sampling container 1 is fitted through the engagement of a circular protrusion 4g that is formed on the outer circumferential surface of the inside plug 4 along the circumferential direction with a circular protrusion 2f that is formed on the inner circumferential surface of the cap 2a along the circumferential direction to seal the inner space of the feces sampling container 1. Note that the lid 2 may be fitted using another means. For example, the lid 2 may be screwed to the inside plug 4 through the engagement of a thread formed on the inner circumferential surface of the cap with a thread formed on the outer circumferential surface of the inside plug 4 (not illustrated in the drawings) as long as it is possible to seal the inner space of the feces sampling container 1.

It is also effective to form a circular protrusion that comes in contact with the edge of the inside plug 4 on the inner surface of the cap 2a (not illustrated in the drawings) in order to improve the sealing capability when the lid 2 is fitted to the container.

The feces sampling container 1 according to one embodiment of the invention is configured so that the inner space of the feces sampling container 1 is sealed by causing the cap 2a to come in contact with the inner circumferential surface of the inside plug 4, while a gap is formed between the outer circumferential surface of the inside plug 4 and the cap 2a. For example, when the feces adhere to the edge of the inside plug 4 by mistake when returning the feces sampling rod 2b to the container after sampling the feces, the feces enter the gap formed between the outer circumferential surface of the inside plug 4 and the cap 2a (i.e., the feces do not flow out from the feces sampling container 1).

It is preferable to produce the lid 2 by integrally forming the cap 2a and the feces sampling rod 2b by injection molding. Note that the cap 2a and the feces sampling rod 2b may be formed separately. A specific configuration of the lid 2 is not particularly limited as long as the lid 2 can seal the inner space of the feces sampling container 1 by the cap 2a, and the feces sampling rod 2b has a hardness sufficient to thrust it into the feces.

The suspension in which the sampled feces are suspended in the preservation solution is discharged through an outlet 3a that is formed on the end of the container body 3 by squeezing the container body 3, and dropped from the dropping cap 5 that is fitted to the end of the container body 3.

Each member of the feces sampling container 1 may be produced by injection molding or the like using a thermoplastic resin such as polypropylene or polyethylene. The container body 3 is produced using a polyolefin resin (e.g., linear low-density polyethylene, low-density polyethylene, or polypropylene) so that the container body 3 can be squeezed. It is preferable to use linear low-density polyethylene from the viewpoint of squeeze capability, water transmission resistance, and injection moldability.

In one embodiment of the invention, the container body 3 is preferably formed to have a cylindrical shape or a tubular shape having an elliptical or oval cross section, and a thin part 3t in which the inner circumferential surface of the side wall is depressed is formed in the vicinity of the end of the container body 3. This makes it possible to easily drop a predetermined amount of suspension by squeezing the container body 3 without impairing the squeeze capability, the strength, and the water transmission resistance of the container body 3.

Figure 4:
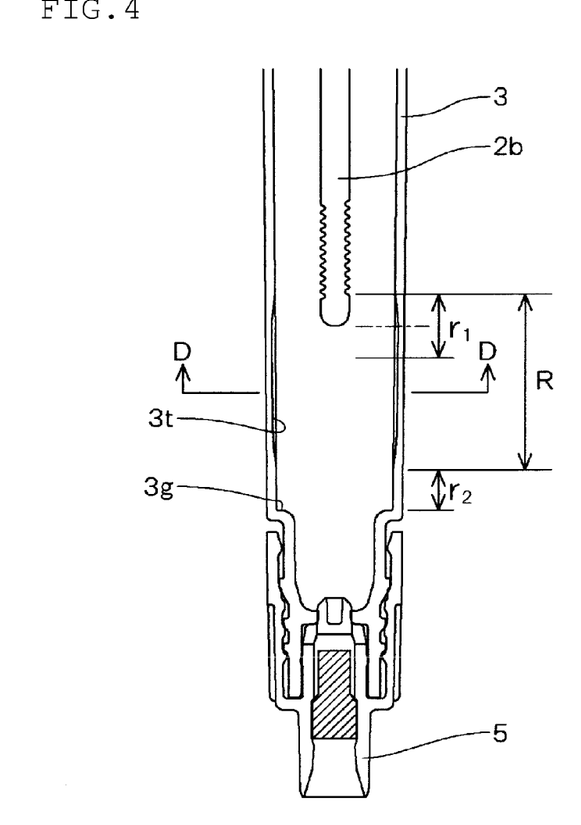
FIG. 4 is an enlarged view illustrating a part illustrated in FIG. 2 that is enclosed by a dash-dotted line.

FIG. 4 is an enlarged view illustrating the part of the feces sampling container 1 illustrated in FIG. 2 that is enclosed by the dash-dotted line.

An area of the container body 3 in which the thin part 3t is formed is selected so that the worker can easily squeeze the container body 3 with fingers, and the container body 3 that has been squeezed and deformed does not interfere with other constituent members. More specifically, it is preferable to form the thin part 3t within a range R from a position that corresponds to the end of the feces sampling rod 2b or the vicinity of the end of the feces sampling rod 2b to a position situated close to a step 3g of the container body 3 in a state in which the inner space of the feces sampling container 1 is sealed with the lid 2, and the dropping cap 5 is fitted to the container body 3.

Note that the position that corresponds to the end of the feces sampling rod 2b or the vicinity of the end of the feces sampling rod 2b refers to a position within a range $r_1$ of about ±10 mm with respect to the end of the feces sampling rod 2b along the longitudinal direction, and the position situated close to the step 3g of the container body 3 refers to a position situated at a distance $r_2$ of about 1 mm or more from the step 3g which formed on the end side of the container body 3 along the longitudinal direction, although the range $r_1$ and the distance $r_2$ may vary depending on the shape and the size of the feces sampling container 1.

Note that the step 3g of the container body 3 is formed as a result of forming a fitting part to which the dropping cap 5 is fitted on the end side of the container body 3.

Figure 5:
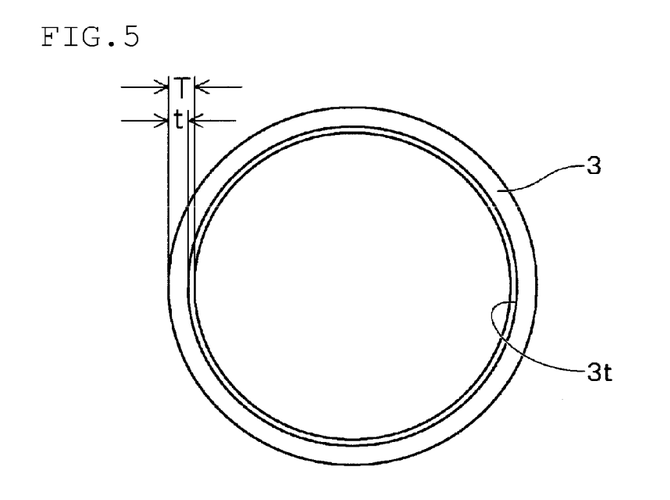
FIG. 5 is a cross-sectional view taken along the line D-D illustrated in FIG. 4.
Figure 6:
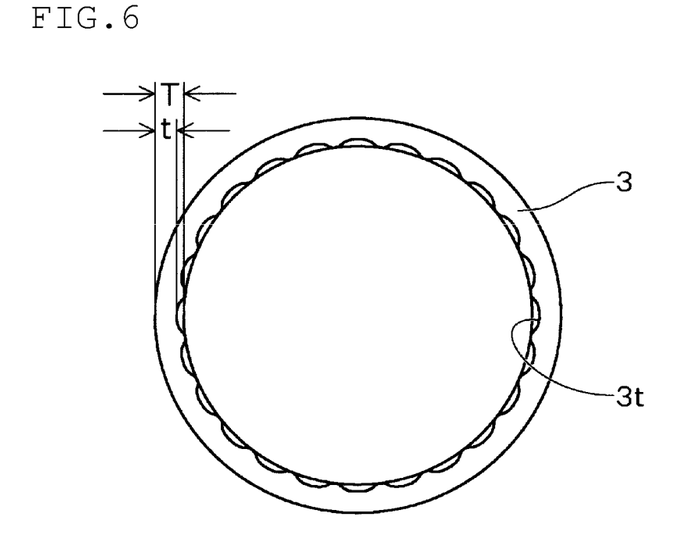
FIG. 6 is a cross-sectional view (that corresponds to FIG. 5) illustrating a modification of a feces sampling container according to one embodiment of the invention.
Figure 7:
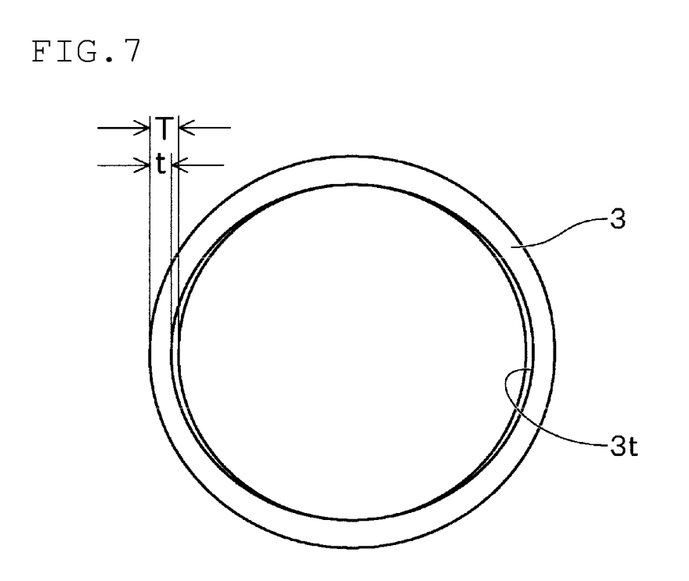
FIG. 7 is a cross-sectional view (that corresponds to FIG. 5) illustrating another modification of a feces sampling container according to one embodiment of the invention.

As illustrated in FIG. 5 (that is a cross-sectional view taken along the line D-D illustrated in FIG. 4), the thin part 3t may be provided over the entire inner circumferential surface of the side wall of the container body 3. Alternatively, a plurality of groove-like thin parts 3t may be formed in the inner circumferential surface of the side wall of the container body 3 so as to extend in the longitudinal direction (see FIG. 6). Alternatively, the thin part 3t may be formed by depressing the inner circumferential surface of the side wall of the container body 3 so as to have an elliptical cross section (see FIG. 7).

The ratio t/T of the thickness t of the thin part 3t to the thickness T of the side wall is preferably 0.2 to 0.95. If the ratio t/T exceeds 0.95, the difference in thickness between the thin part 3t and the remaining part is small, and it may be difficult to obtain the advantageous effects of the invention. If the ratio UT is less than 0.2, the fluidity of a molten resin when producing the container body 3 by injection molding may be impaired, and the container body 1 may exhibit insufficient strength.

In one embodiment of the invention, the container body 3 includes a partition wall 3b which is situated on the end of the container body 3 and in which the outlet 3a is formed.

The dropping cap 5 that is fitted to the end side of the container body 3 by screwing (screw tightening) includes a sealing body 5a that seals the outlet 3a. The feces sampling container 1 according to one embodiment of the invention is thus configured so that the outlet 3a is opened by loosening the dropping cap 5 (see FIG. 2), and re-sealed by re-tightening the dropping cap 5.

Note that FIG. 2 is a cross-sectional view taken along the line A-A illustrated in FIG. 1 in a state in which the dropping cap 5 has been loosened.

In one embodiment of the invention, a first circular protrusion 3d is formed on the outer circumferential surface of the end side of the container body 3 (to which the dropping cap 5 is fitted) at a predetermined position along the circumferential direction. A second circular protrusion 5b is formed on the inner circumferential surface of the dropping cap 5 at a predetermined position along the circumferential direction.

The position at which the first circular protrusion 3d is formed on the outer circumferential surface of the end side of the container body 3, and the position at which the second circular protrusion 5b is formed on the inner circumferential surface of the dropping cap 5, are appropriately adjusted so that the first circular protrusion 3d and the second circular protrusion 5b come in contact with each other when the sealing body 5a has moved away from the outlet 3a and the outlet 3a has been opened as a result of loosening the dropping cap 5 (see FIG. 2). According to this configuration, it is possible to perceive that the feces sampling container 1 has been opened by feeling that the first circular protrusion 3d and the second circular protrusion 5b have came in contact with each other, and prevent a situation in which the dropping cap 5 falls as a result of loosening the dropping cap 5 to a large extent.

In one embodiment of the invention, a body-side thread 3e is formed on the outer circumferential surface of the end side of the container body 3, and a cap-side thread 5c is formed on the inner circumferential surface of the dropping cap 5 so that the dropping cap 5 can be screwed to the container body 3. It is preferable to form the body-side thread 3e of the container body 3 and the cap-side thread 5c of the dropping cap 5 so that either or both of the body-side thread 3e and the cap-side thread 5c are decreased in height or removed within a range in which the body-side thread 3e and the cap-side thread 5c engage with each other in a state in which the first circular protrusion 3d and the second circular protrusion 5b come in contact with each other, such that the body-side thread 3e and the cap-side thread 5c can climb over each other.

Figure 8:
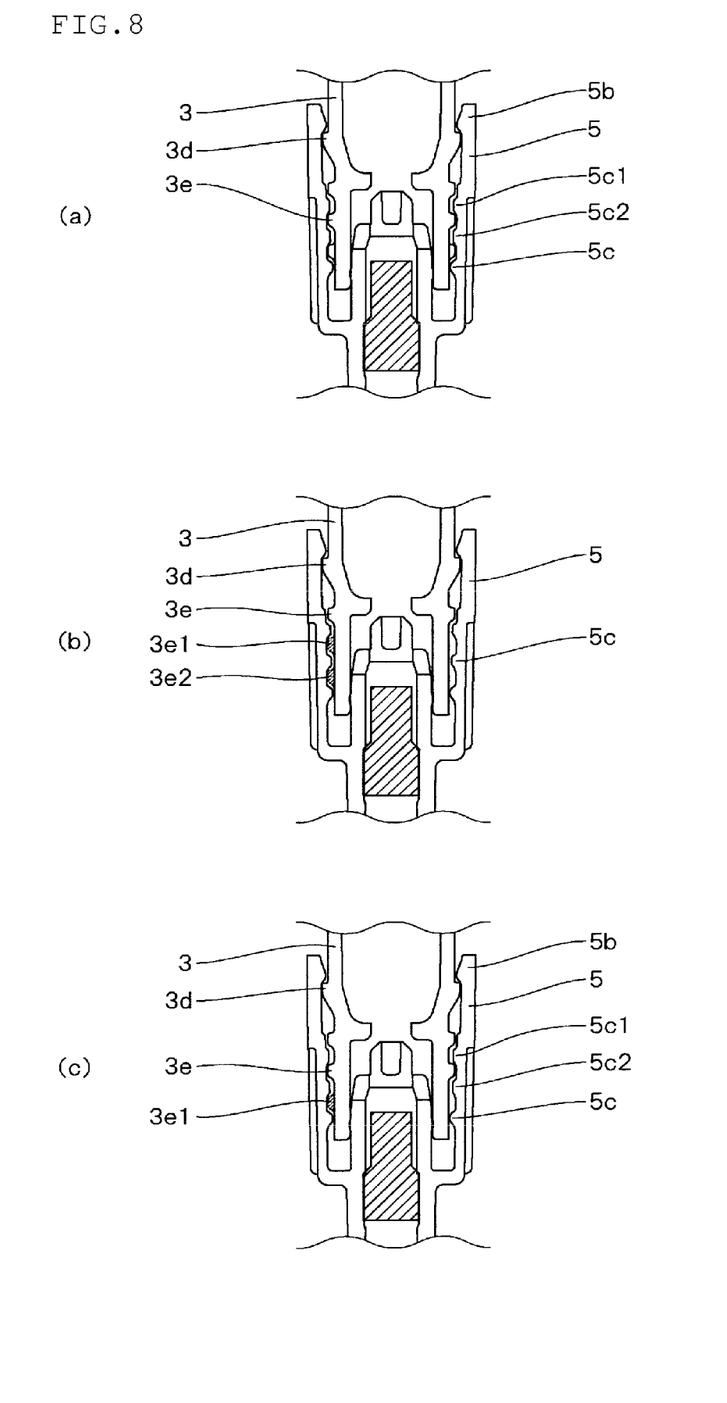
FIG. 8 is a reference cross-sectional view illustrating an example of a screwed state of a dropping cap included in a feces sampling container according to one embodiment of the invention.

FIG. 8 illustrates an example of a configuration in which the body-side thread 3e of the container body 3 and the cap-side thread 5c of the dropping cap 5 can climb over each other.

FIG. 8(a) illustrates an example in which the cap-side thread 5c of the dropping cap 5 is decreased in height within a range from thread $5c_1$ to $5c_2$ situated on the side of the second circular protrusion 5b. FIG. 8(b) illustrates an example in which the body-side thread 3e of the container body 3 is removed within a range from thread $3e_1$ to $3e_2$ (indicated by the dot-dash lines) situated away from the first circular protrusion 3d. FIG. 8(c) illustrates an example in which the body-side thread 3e of the container body 3 is removed within a range of thread $3e_1$ (indicated by the dot-dash lines), and the cap-side thread 5c of the dropping cap 5 is decreased in height within a range from thread $5c_1$ to $5c_2$.

In such a case, when the feces sampling container 1 has been opened, and the first circular protrusion 3d and the second circular protrusion 5b have come in contact with each other, the dropping cap 5 runs idle with respect to the container body 3. Due to such idling of the dropping cap 5 with respect to the container body 3, examination is performed without removing the dropping cap 5 from the container body 3, and it is possible to prevent a situation in which the dropping cap required for re-sealing is lost.

Figure 9:
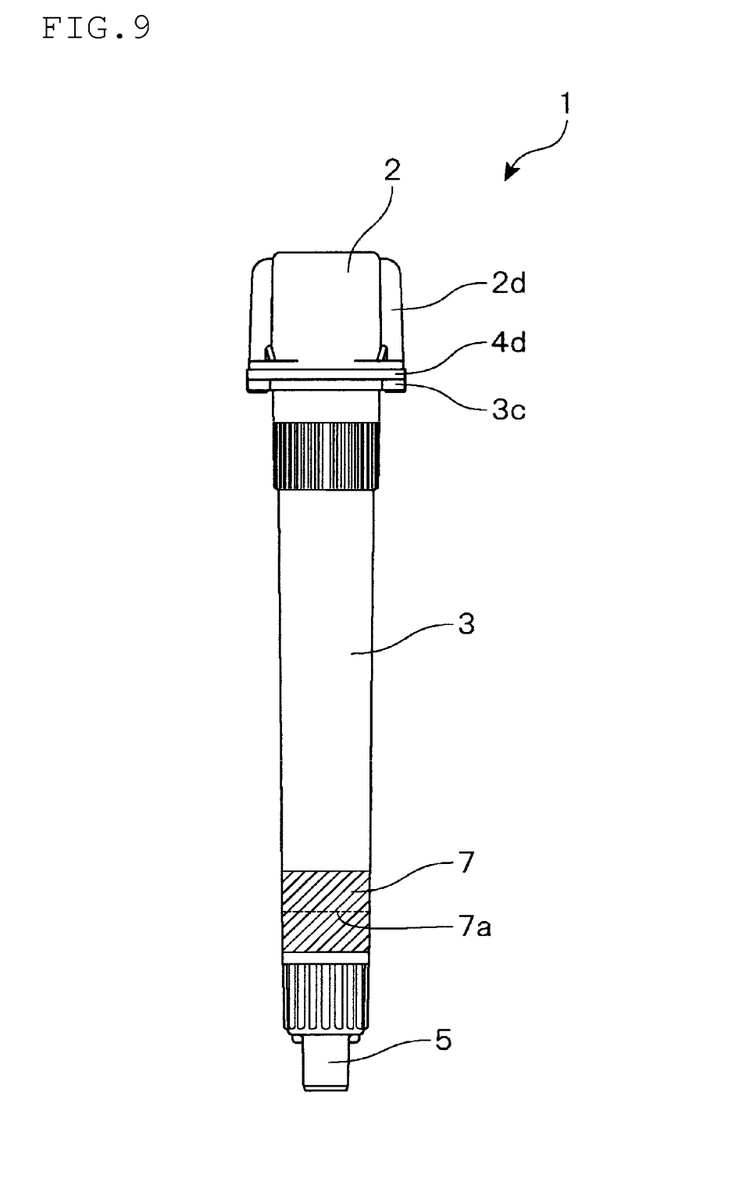
FIG. 9 is a front view illustrating another example of a feces sampling container according to one embodiment of the invention.

In one embodiment of the invention, it is preferable to wind a tape-like member 7 (in which a perforated line 7a is formed along the circumferential direction) (see FIG. 9) around the feces sampling container 1 so that the perforated line 7a is situated at the boundary between the container body 3 and the dropping cap 5. This makes it possible to prevent a situation in which the dropping cap 5 loosens before the feces sampling container 1 is opened (before examination), and easily determine whether or not the feces sampling container 1 has been opened.

The base end side of the container body 3 is open so that the inside plug 4 can be fitted to the inside of the container body 3. The inner circumferential surface of the container body 3 and the outer circumferential surface of the inside plug 4 liquid-tightly come in contact with each other when the inside plug 4 is fitted to the inside of the container body 3 so that leakage of the preservation solution held in the container body 3 does not occur.

Figure 10:
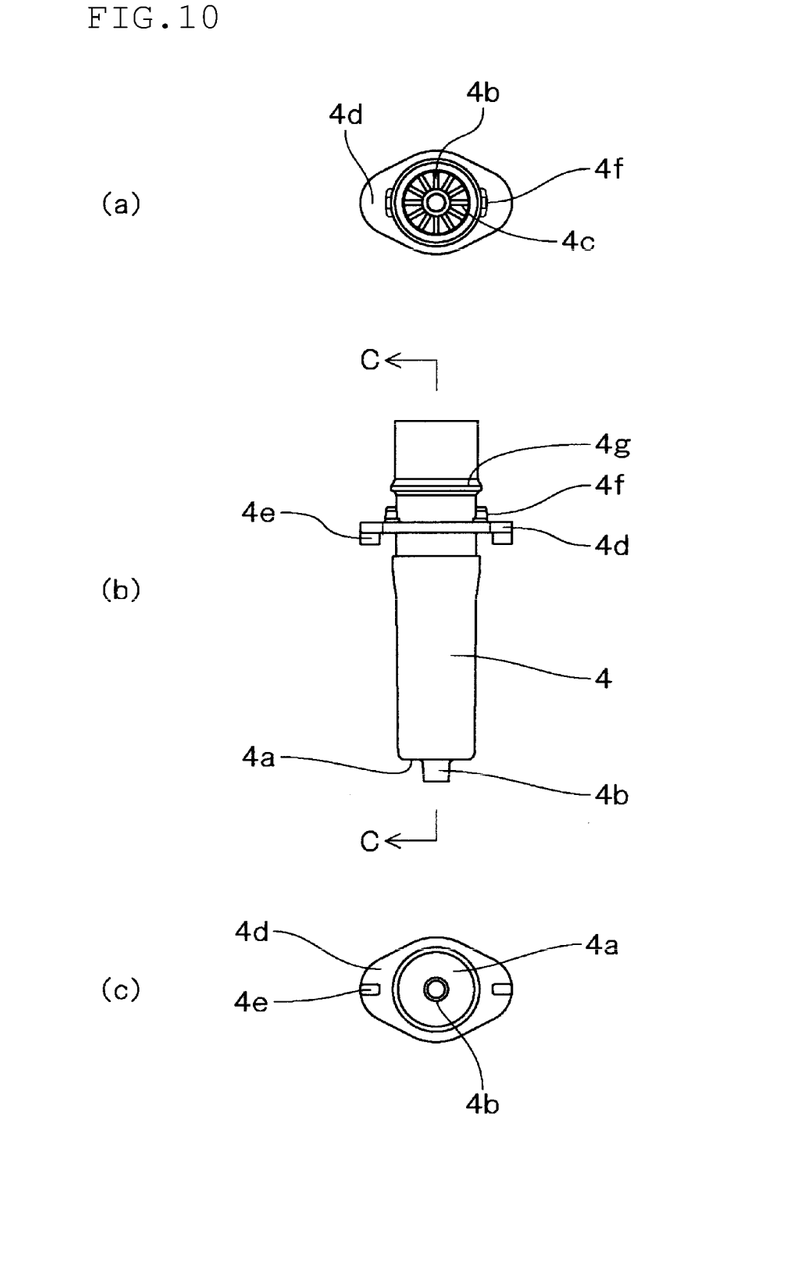
FIG. 10 is a view illustrating an example of an inside plug included in a feces sampling container according to one embodiment of the invention, wherein (a) is a plan view, (b) is a front view, and (c) is a bottom view.
Figure 11:
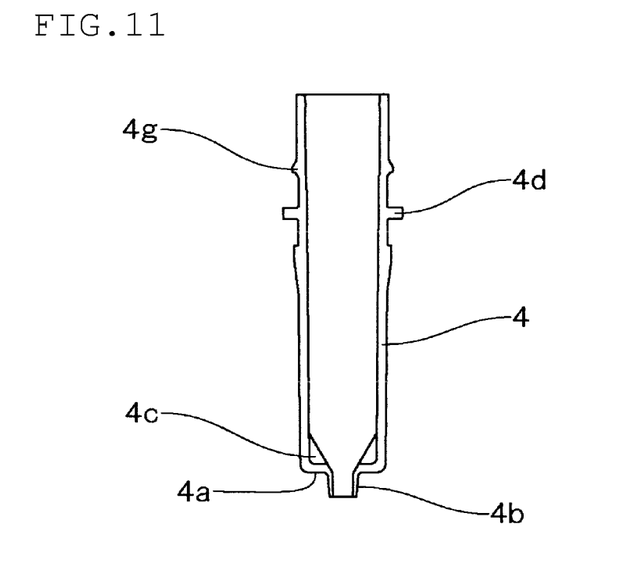
FIG. 11 is a cross-sectional view taken along the line C-C illustrated in FIG. 10 (see (b)).

As illustrated in FIGS. 10 and 11, the end of the inside plug 4 that is fitted to the inside of the container body 3 has a bottom surface 4a that extends in the direction orthogonal to the longitudinal direction, and a removal part 4b into which the feces sampling rod 2 of the lid 2b can be inserted is formed at the center of the bottom surface 4a. The removal part 4b is designed to remove excess feces that adhere to the feces sampling rod 2b when the feces sampling rod 2b is returned to the container body 3 after the feces have been sampled. In one embodiment of the invention, the removal part 4b is formed in the shape of a tube that opens at the center of the bottom surface 4a. The removal part 4b is formed so that excess feces are removed when the feces sampling rod 2b liquid-tightly comes in contact with the inner circumferential surface of the removal part 4b, and slides on the inner circumferential surface of the removal part 4b. This makes it possible to suspend a predetermined amount of feces with which the helical groove 2c is filled in the preservation solution held in the container body 3.

The inside plug 4 constituting the removal part 4b may have a tapered outer shape in which the diameter of the inside plug 4 gradually decreases toward the removal part 4b from the middle of the inside plug 4 so that the feces sampling rod 2b can be reliably guided to the removal part 4b.

In this case, however, a gap is formed between the side of the tapered part and the inner surface of the container body 3, whereby the volume of the preservation solution-holding part increases. If the volume of the preservation solution-holding part is too large, the end of the feces sampling rod 2b may be exposed to air when the feces sampling container 1 is stored horizontally (or stored in a state in which the dropping cap 5 is situated on the upper side) after the feces have been sampled, whereby the stability of the measurement target components included in the feces may be impaired. Therefore, it is preferable to form the inside plug 4 to have a shape that reduces the volume of the preservation solution-holding part as much as possible.

Accordingly, it is preferable to form the inside plug 4 to have an approximately cylindrical outer shape, and form the bottom surface 4a to have a flat shape that is orthogonal to the longitudinal direction, or to have a shape that is depressed from the periphery toward the removal part 4b that is situated at the center.

In one embodiment of the invention, a feces sampling rod guide that includes a plurality of tilted ribs 4c that are provided radially is formed around the removal part 4b so that the feces sampling rod 2b can be easily inserted into the removal part 4b when the feces sampling rod 2b is returned to the inside of the container body 3 after the feces have been sampled.

In one embodiment of the invention, the tilted ribs 4c are formed so as to form a triangular shape that has a side that extends diagonally from the edge of the removal part 4b. Note that the shape of the tilted ribs 4c is not particularly limited as long as the feces sampling rod 2b can be guided to the removal part 4b.

The feces sampling rod 2b can be guided to the removal part 4b by forming a cone-shaped part around the removal part 4b. In this case, however, since the thickness of the side of the bottom surface 4a of the end of the inside plug 4 increases, the amount of resin required to form the inside plug 4 increases, and it takes time to cool the product (i.e., the production speed decreases). Moreover, the amount of shrinkage of the resin during cooling increases, and deterioration in dimensional stability occurs. The feces sampling rod guide can be formed by disposing a plurality of tilted ribs 4c radially and providing a space between adjacent the tilted ribs 4c, thereby such disadvantages can be effectively eliminated.

The feces sampling container 1 according to one embodiment of the invention is opened by loosening the dropping cap 5 after suspending the feces sampled using the feces sampling rod 2b in the preservation solution held in the container body 3. The suspension obtained by suspending the feces in the preservation solution is discharged through the outlet 3a provided on the end of the container body 3 by squeezing the container body 3, and filtered through a filter 6 that is provided to the dropping cap 5, and the filtrate is dropped and subjected to examination.

A material for forming the filter 6 that is provided to the dropping cap 5 is not particularly limited as long as the filter 6 can remove a solid that hinders the examination from the suspension, and is inert to the examination target. Examples of the material for forming the filter 6 include a porous substance (e.g., Moltofilter, paper filter, and sintered resin filter), a fibrous substance (e.g., glass wool and absorbent cotton), and the like. It is preferable to use a Moltofilter or a sintered resin filter having a predetermined pore size. The filter 6 may include only one type of filter, or may be formed by stacking two or more types of filters.

An arbitrary preservation solution that is suitable for fecal examination may be used as the preservation solution in which the sampled feces are suspended. An additive such as a buffer, a stabilizer, a preservative, a dye, or an odor absorber may optionally be added to the preservation solution. The amount of the preservation solution held in the container body is appropriately adjusted corresponding to the feces suspension concentration required for fecal examination. For example, when sampling 5 mg of feces, a dilution ratio of 400 is obtained by adjusting the amount of the preservation solution to 2 ml.

Figure 12:
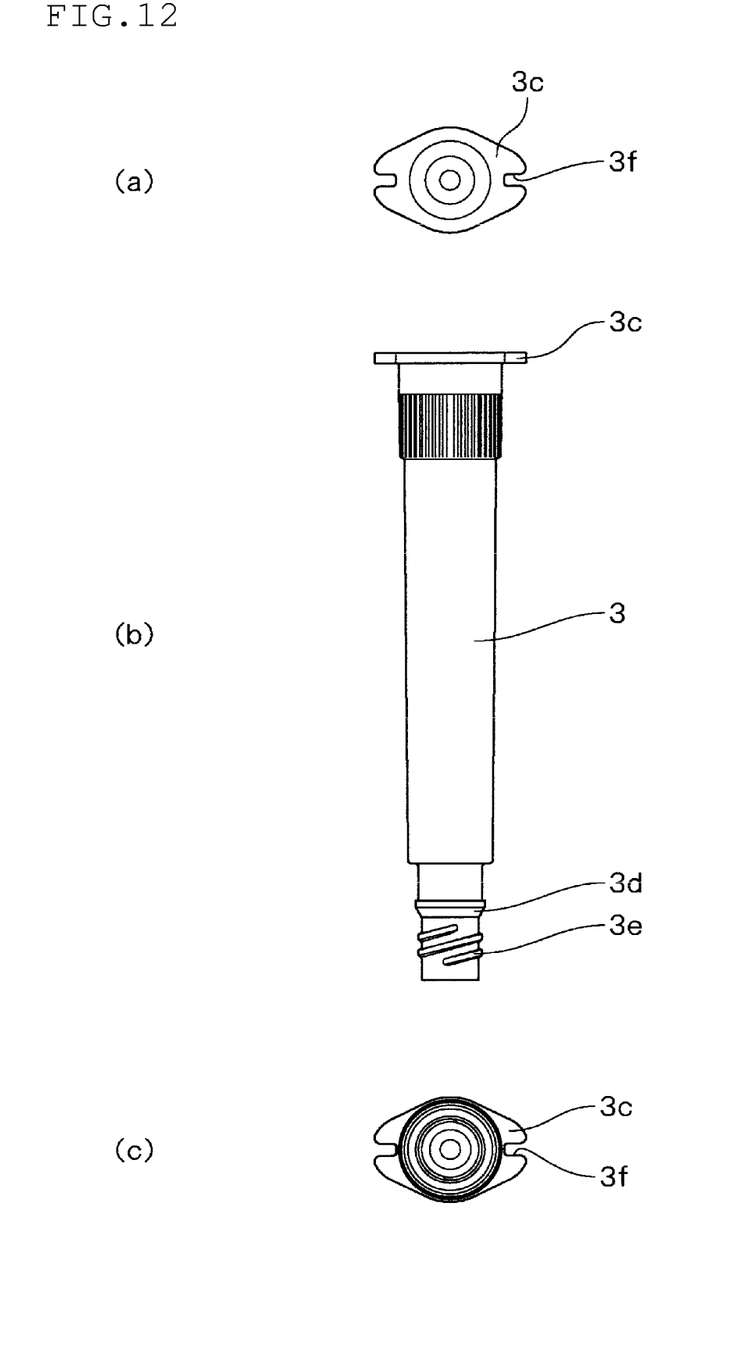
FIG. 12 is a view illustrating an example of a container body included in a feces sampling container according to one embodiment of the invention, wherein (a) is a plan view, (b) is a front view, and (c) is a bottom view

In one embodiment of the invention, a flange 3c is formed along the edge of the base end-side opening of the container body 3 (see FIG. 12). An overhang 4d is formed on the outer circumferential surface of the inside plug 4 (see FIG. 10) along the circumferential direction at a position at which the overhang 4d is situated on the flange 3c of the container body 3 when the inside plug 4 is fitted to the inside of the container body 3.

In one embodiment of the invention, since the removal part 4b with which the feces sampling rod 2b liquid-tightly comes in contact and which removes excess feces is formed on the end of the inside plug 4, it is preferable to form the inside plug 4 using a hard material. The container body 3 may be formed using a soft material taking account of the squeeze capability. In this case, the container body 3 and the inside plug 4 are formed using different types of materials that are difficult to weld. Therefore, when securing the inside plug 4 that is fitted to the inside of the container body 3, it is desirable to prevent a situation in which the inside plug 4 rotates with respect to the container body 3, or the inside plug 4 rotates together with the lid 2 when fitting or removing the lid 2 to or from the inside plug 4. In one embodiment of the invention, an engagement part that is formed by a notch 3f is provided to the flange 3c formed on the container body 3, and a locking part that is formed by a protrusion 4e that engages with the notch 3f is provided to the overhang 4d formed on the inside plug 4 (see the drawings) to prevent a situation in which the inside plug 4 rotates with respect to the container body 3, or the inside plug 4 rotates together with the lid 2 when fitting or removing the lid 2 (having the feces sampling rod 2b) to or from the inside plug 4.

Note that the engagement part that is provided to the flange 3c formed on the container body 3 may be formed by a groove, a through-hole, or the like instead of the notch 3f, and the shape of the locking part provided to the overhang 4d formed on the inside plug 4 may be appropriately selected corresponding to the shape of the engagement part. The engagement part may be provided to the overhang 4d formed on the inside plug 4, and the locking part may be provided to the flange 3c formed on the container body 3.

It is preferable to form the flange 3c that is formed on the container body 3 and the overhang 4d that is formed on the inside plug 4 to have a diamond shape (see the drawings), an elliptical shape, a track shape, or the like (i.e., a shape that is longer in one of two orthogonal directions) in order to prevent the rolling of the feces sampling container 1 during examination.

As illustrated in FIG. 3, blades 2d that make a pair and make it possible to easily turn the lid 2 are symmetrically formed on the cap 2a of the lid 2, and the side of the lower end of the cap 2a of the lid 2 situated at the lower end side of each blade 2d is partially swelled (expanded) to form a hollow to symmetrically form sloping grooves 2e that make a pair and slope outward in the downward direction (on the upper end). As illustrated in FIG. 10, sloping protrusions 4f that make a pair and slope outward in the downward direction (at least on the upper end side) are symmetrically formed on the major axis-side inner circumferential surface of the overhang 4d of the inside plug 4. According to this configuration, it is possible to turn the lid 2 while holding the blades 2d of the lid 2 with fingers to easily remove the lid 2 from the inside plug 4 by utilizing a removal mechanism that is formed by the sloping groove 2e of the lid 2 and the sloping protrusion 4f of the inside plug 4.

Note that it is preferable that the upper part of each side of the sloping groove 2e of the lid 2 and the upper part of each side of the sloping protrusion 4f of the inside plug 4 that form the removal mechanism have an identical shape (preferably a linear shape or a curved shape (concave shape)) so that the lid 2 can be turned smoothly in an arbitrary direction.

Although an example in which the sloping grooves 2e that make a pair are symmetrically provided to the lid 2, and the sloping protrusions 4f that make a pair are symmetrically provided to the inside plug 4 has been described above, only one sloping groove 2e may be provided to the lid 2, or only one sloping protrusion 4f may be provided to the inside plug 4. The sloping groove 2e that is formed in the lid 2 may be provided to the side of the lower end of the cap 2a that is orthogonal to the blade 2d, and the sloping protrusion 4f that is formed on the inside plug 4 may be provided to the minor axis-side inner circumferential surface of the overhang 4d. Note that it is preferable to form the sloping groove 2e at the lower end side of the blade 2d of the cap 2a of the lid 2, and form the sloping protrusion 4f on the major axis-side inner circumferential surface of the overhang 4d of the inside plug 4 since it is easy to form the sloping groove 2e and the sloping protrusion 4f.

Figure 13:
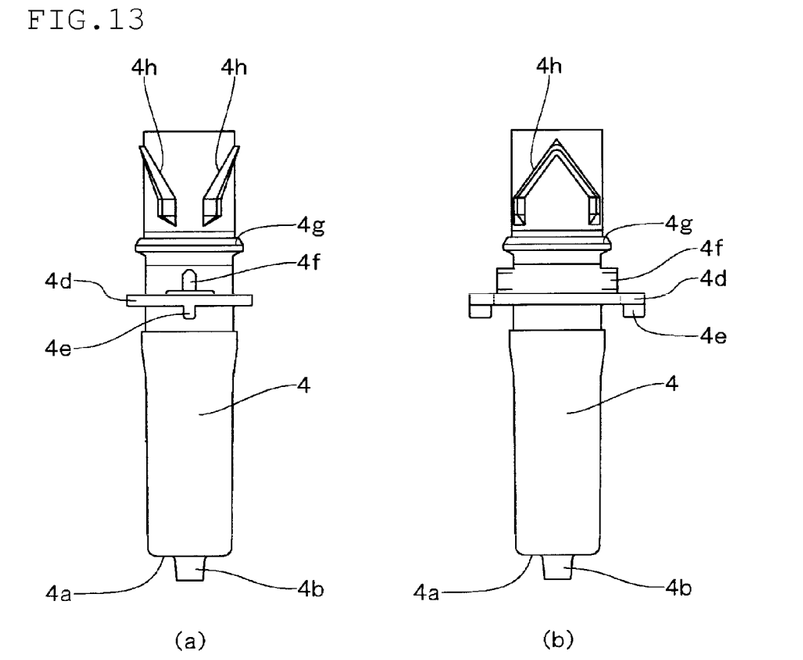
FIG. 13 is a view illustrating another example of an inside plug included in a feces sampling container according to one embodiment of the invention, wherein (a) is a side view, and (b) is a front view.
Figure 14:
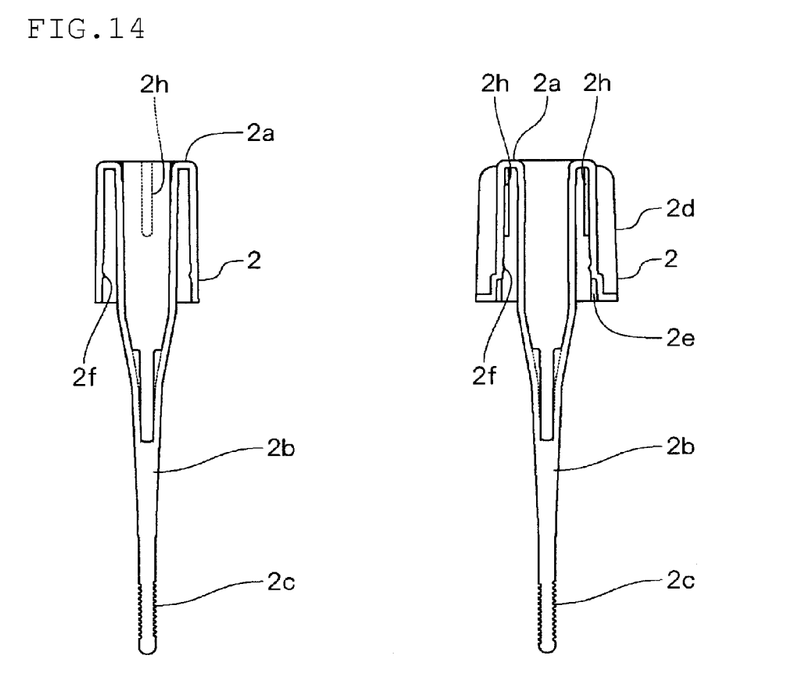
FIG. 14 is a view illustrating a lid applied to another example of an inside plug included in a feces sampling container according to one embodiment of the invention, wherein (a) is a minor axis-side cross-sectional view illustrating the lid, and (b) is a major axis-side cross-sectional view illustrating the lid.

In this case, when fitting the lid 2 to the inside plug 4, the sloping groove 2e of the lid 2 and the sloping protrusion 4f of the inside plug 4 that form the removal mechanism are positioned, and the circular protrusion 2f formed on the inner circumferential surface of the cap 2a of the lid 2 and the circular protrusion 4g formed on the outer circumferential surface of the inside plug 4 engage with each other. As illustrated in FIG. 13, guide cams 4h that make a pair and slope downward with respect to the axial direction from the apex side to form an inverted V-like shape (so that the lower end preferably extends parallel to the axial direction) are symmetrically formed over the circular protrusion 4g of the inside plug 4. As illustrated in FIG. 14, elongated protrusions 2h that make a pair and extend along the axial direction are symmetrically formed over the circular protrusion 2f of the cap 2a of the lid 2. The guide cam 4h of the inside plug 4 and the elongated protrusion 2h of the lid 2 form a cam mechanism, and the elongated protrusion 2h of the lid 2 is guided by the guide cam 4h of the inside plug 4 when pushing the lid 2 having the feces sampling rod 2b into the inside plug 4 while turning the lid 2. This makes it possible to easily and reliably fit the lid 2 to the inside plug 4 in a state in which the sloping groove 2e of the lid 2 and the sloping protrusion 4f of the inside plug 4 that form the removal mechanism engage with each other.

When the flange 3c that is formed on the container body 3 and the overhang 4d that is formed on the inside plug 4 have a shape that is longer in one of two orthogonal directions, and the blade 2d is formed on the cap 2a of the lid 2, it is preferable to form the guide cam 4h of the inside plug 4 that forms the cam mechanism on the minor axis side of the overhang 4d of the inside plug 4, and form the elongated protrusion 2h of the lid 2 at the same position as the blade 2d and the sloping groove 2e of the cap 2a. According to this configuration, it is possible to prevent a situation in which the cap 2a of the lid 2 sinks during molding, and ensure that the blade 2d formed on the cap 2a is positioned on the major axis side of the flange 3c formed on the container body 3 and the overhang 4d formed on the inside plug 4.

Although an example in which the elongated protrusions 2h are symmetrically provided to the lid 2, and the guide cams 4h are symmetrically provided to the inside plug 4 has been described above, only one elongated protrusion 2h may be provided to the lid 2, or only one guide cam 4h may be provided to the inside plug 4. Note that it is preferable to symmetrically form a pair of elongated protrusions 2h and a pair of guide cams 4h from the viewpoint of the engagement of the lid 2 with the inside plug 4, and ease and stability of immobilization. The guide cam 4h of the inside plug 4 may be formed on the major axis side of the overhang 4d, and the elongated protrusion 2h of the lid 2 may be formed to be orthogonal to the blade 2d and the sloping groove 2e.

The preferred embodiments of the invention have been described above. Note that the invention is not limited to the above embodiments, and various modifications and variations may be made without departing from the scope of the invention.

Although the above embodiments have been described taking an example in which the removal part 4b is provided inside the container body 3 by fitting the inside plug 4 provided with the removal part 4b to the inside of the container body 3, the inside plug 4 may be omitted, and the removal part 4b may be formed directly inside the container body 3.

INDUSTRIAL APPLICABILITY

As described above, the invention can be applied to a feces sampling container that is used to sample feces that are subjected to fecal examination.

REFERENCE SIGNS LIST

1 Feces sampling container
2 Lid
2a Cap
2b Feces sampling rod
2d Blade
2e Sloping groove
2f Circular protrusion
2h Elongated protrusion
3 Container body
3a Outlet
3c Flange
3d First circular protrusion
3e Body-side thread
3f Notch
3g Step
3t Thin part
4 Inside plug
4a Bottom surface
4b Removal part
4c Tilted rib
4d Overhang
4e Protrusion
4f Sloping protrusion
4g Circular protrusion
4h Guide cam
5 Dropping cap
5a Sealing body
5b Second circular protrusion
5c Cap-side thread
7 Tape-like member
7a Perforated line

The invention claimed is:

1. A feces sampling container comprising:
   a lid that comprises a feces sampling rod and a cap, a circular protrusion being formed on an inner circumferential surface of the cap along a circumferential direction;
   a container body that has a tubular shape and opens on a base end side; and
   an inside plug that comprises a removal part and a circular protrusion, the circular protrusion being formed on an outer circumferential surface of the inside plug along a circumferential direction, the inside plug being fitted to inside of the container body through the base end side of the container body,
   a flange being formed along an edge of a base end side opening of the container body,
   an overhang being formed on an outer circumferential surface of the inside plug at a given position along a circumferential direction so that the overhang is situated on the flange,
   a removal mechanism which comprises a sloping groove that is formed at a lower end of the cap and a sloping protrusion that is formed on an inner circumferential surface of the overhang of the inside plug, and
   a cam mechanism that positions the removal mechanism, said cam mechanism comprising an elongated protrusion that is formed over the circular protrusion formed on the inner circumferential surface of the cap and a guide cam that is formed over the circular protrusion formed on the outer circumferential surface of the inside plug.

2. The feces sampling container according to claim 1, wherein the flange and the overhang are formed to have a shape that is longer in one of two orthogonal directions.

3. The feces sampling container according to claim 2, wherein blades that make a pair are symmetrically formed on the cap of the lid.

4. The feces sampling container according to claim 1, wherein the sloping groove is formed by partially swelling a side of the lower end of the cap to form a hollow, and slopes outward in a downward direction on an upper end side, and the sloping protrusion slopes outward in a downward direction at least on an upper end side.

5. The feces sampling container according to claim 3, wherein the sloping groove is formed at a lower end side of the blade of the cap, and the sloping protrusion is formed on a major axis-side inner circumferential surface of the overhang of the inside plug.

6. The feces sampling container according to claim 1, wherein the guide cam slopes downward with respect to an axial direction from the apex side to form an inverted V-like shape, and the elongated protrusion extends along an axial direction.

7. The feces sampling container according to claim 3, wherein the guide cam is formed on a minor axis side of the overhang of the inside plug, and the elongated protrusion is formed at the same position as each of the blades and the sloping groove of the cap.

8. The feces sampling container according to claim 1, wherein the removal mechanisms that make a pair and the cam mechanisms that make a pair are respectively formed symmetrically.

9. The feces sampling container according to claim 1, wherein an engagement part is provided to one of the flange and the overhang, and a locking part that is fitted to the engagement part is provided to the other of the flange and the overhang.

10. The feces sampling container according to claim 9, wherein the engagement part is a notch, and the locking part is a protrusion.

11. The feces sampling container according to claim 1, wherein an end of the inside plug has a bottom surface that extends in a direction orthogonal to a longitudinal direction, a removal part is formed at a center of the bottom surface, and a feces sampling rod guide that comprises a plurality of tilted ribs that are provided radially is formed around the removal part.

12. The feces sampling container according to claim 1, wherein an outlet is formed on an end side of the container body, and a dropping cap that comprises a sealing body that seals the outlet is screwed to the container body.

13. The feces sampling container according to claim 12, wherein a first circular protrusion, different from the circular protrusion formed on an inner circumferential surface of the cap and the circular protrusion formed on the outer circumferential surface of the inside plug, is formed on an outer circumferential surface of an end side of the container body at a predetermined position along a circumferential direction, a second circular protrusion, different from the circular protrusion formed on an inner circumferential surface of the cap and the circular protrusion formed on the outer circumferential surface of the inside plug, is formed on an inner circumferential surface of the dropping cap at a predetermined position along a circumferential direction, and the first circular protrusion and the second the circular protrusion come in contact with each other to prevent the dropping cap from falling when the dropping cap is loosened so that the sealing body moves away from the outlet and the outlet is opened.

14. The feces sampling container according to claim 13, wherein a body-side thread is formed on the outer circumferential surface of the end side of the container body to which the dropping cap is screwed, and a cap-side thread is formed on the inner circumferential surface of the dropping cap so that either or both of the body-side thread and the cap-side thread are decreased in height or removed within a range in which the body-side thread and the cap-side thread engage with each other in a state in which the first circular protrusion and the second circular protrusion come in contact with each other, such that the body-side thread and the cap-side thread can climb get over each other.

15. The feces sampling container according to claim 12, wherein a tape member in which a perforated line is formed along a circumferential direction is wound around the feces sampling container so that the perforated line is situated at a boundary between the container body and the dropping cap.

16. The feces sampling container according to claim 12, wherein a thin part in which an inner circumferential surface of a side wall is depressed is formed in a vicinity of an end of the container body.

17. The feces sampling container according to claim 16, wherein the thin part is formed within a range from a position that corresponds to an end of the feces sampling rod or a vicinity of the end of the feces sampling rod to a position situated close to a step of the container body in a state in which an inner space of the feces sampling container is sealed with the lid, and the dropping cap is fitted to the container body.

18. The feces sampling container according to claim 16, wherein the container body is formed using linear low-density polyethylene, low-density polyethylene, or polypropylene.

* * * * *